United States Patent
Dietz et al.

[11] Patent Number: 5,984,088
[45] Date of Patent: *Nov. 16, 1999

[54] EASY OPEN PACKAGE AND METHOD OF MAKING SAME

[75] Inventors: Peter T. Dietz, Eagan; Gregory R. Lambach, South St. Paul; Mark R. Montbriand, North St. Paul, all of Minn.

[73] Assignee: 3M Innovative Properties Company, St. Paul, Minn.

[ * ] Notice: This patent is subject to a terminal disclaimer.

[21] Appl. No.: 08/795,178

[22] Filed: Feb. 4, 1997

Related U.S. Application Data

[63] Continuation-in-part of application No. 08/402,512, Mar. 10, 1995, Pat. No. 5,620,095, and a continuation-in-part of application No. 08/075,663, Jun. 11, 1993, abandoned.

[51] Int. Cl.$^6$ ................................................. B65D 65/36
[52] U.S. Cl. .......................... 206/205; 206/438; 383/201
[58] Field of Search ................................. 206/438, 484, 206/210, 205; 229/313–316; 383/200, 201, 207–209

[56] References Cited

U.S. PATENT DOCUMENTS

| | | | |
|---|---|---|---|
| 2,307,735 | 1/1943 | Fehr | 229/51 |
| 2,578,324 | 12/1951 | Southwick, Jr. | 183/4.8 |
| 2,956,723 | 10/1960 | Tritsch | 229/48 |
| 3,084,984 | 4/1963 | Adler | 312/31 |
| 3,127,087 | 3/1964 | Spees | 229/5 |
| 3,272,424 | 9/1966 | Rodkey | 229/66 |
| 3,323,707 | 6/1967 | King | 229/66 |
| 3,485,349 | 12/1969 | Chaney, Jr. | 206/56 |
| 3,494,538 | 2/1970 | Matthews | 229/51 |
| 3,535,409 | 10/1970 | Rohde | 264/95 |
| 3,554,436 | 1/1971 | Palmer | 229/62 |
| 3,595,468 | 7/1971 | Repko | 229/66 |
| 3,608,566 | 9/1971 | Storandt | 132/84 |

(List continued on next page.)

FOREIGN PATENT DOCUMENTS

| | | | |
|---|---|---|---|
| 0 089 680 | 9/1983 | European Pat. Off. | B65D 33/00 |
| 0 407 056 | 1/1991 | European Pat. Off. | A61L 15/07 |
| 0 450 247 A2 | 9/1991 | European Pat. Off. | |
| 0 471 220 | 2/1992 | European Pat. Off. | B29C 47/06 |
| 0 522 824 | 1/1993 | European Pat. Off. | A61F 13/04 |
| 40 00 857 | 7/1991 | Germany | B65D 17/28 |
| 41 09 605 | 9/1992 | Germany | B65D 75/62 |
| 43 05 662 | 9/1993 | Germany | B65D 30/02 |
| 56-123256 | 9/1981 | Japan | B65D 33/00 |
| 59-26450 | 2/1984 | Japan | B65D 33/00 |
| 60-13661 | 1/1985 | Japan | B65D 77/30 |
| 8600546 | 10/1987 | Netherlands | B65D 65/34 |
| 384 452 | 11/1964 | Switzerland | |
| 715997 | 9/1954 | United Kingdom | 94/1 |
| 2 200 286 | 8/1988 | United Kingdom | A61F 13/04 |
| WO 86/02908 | 5/1986 | WIPO | B65D 75/58 |
| WO 92/16431 | 10/1992 | WIPO | B65D 75/58 |

OTHER PUBLICATIONS

International Search Report for PCT/US/98/02050.

Noller; "Chemistry of Organic Compounds"; Ch. 6, pp. 121–122 (1957).

Photocopy of a package sold under trade name "CELLA-CAST XTRA".

*Primary Examiner*—Jim Foster
*Attorney, Agent, or Firm*—Eloise J. Maki

[57] ABSTRACT

The present invention provides kits of orthopedic casting materials comprising a sheet of curable casting material, a lubricant, and an air and water impermeable package comprising a laminate sheet material and a means for facilitating tearing of the sheet material when the outer surface of the pouch has been contacted with the lubricant. In a preferred embodiment of the present invention the means for facilitating the tearing of the sheet comprises a matte-finish paper label material adhered to the outer surface of the package and crossing a cut. In another preferred embodiment of the present invention the means for facilitating the tearing of the sheet comprises a plurality of perforations through the sealed portion of the package adjacent a cut.

14 Claims, 3 Drawing Sheets

U.S. PATENT DOCUMENTS

| | | | |
|---|---|---|---|
| 3,630,194 | 12/1971 | Boardman | 128/90 |
| 3,648,704 | 3/1972 | Jackson | 128/349 |
| 3,759,439 | 9/1973 | Cross et al. | 229/66 |
| 3,770,122 | 11/1973 | Thiele | 206/84 |
| 3,873,735 | 3/1975 | Chalin et al. | 426/87 |
| 3,908,644 | 9/1975 | Neimart et al. | 128/90 |
| 3,932,526 | 1/1976 | Koshar | 260/607 |
| 4,131,114 | 12/1978 | Kirkpatrick et al. | 128/90 |
| 4,139,643 | 2/1979 | Hix et al. | 426/122 |
| 4,246,288 | 1/1981 | Sanborn, Jr. | 426/122 |
| 4,279,344 | 7/1981 | Holloway, Jr. | 206/631 |
| 4,411,262 | 10/1983 | von Bonin et al. | 128/90 |
| 4,433,680 | 2/1984 | Yoon | 128/90 |
| 4,441,262 | 4/1984 | Gazzoni | 34/57 |
| 4,502,479 | 3/1985 | Garwood et al. | 128/90 |
| 4,598,826 | 7/1986 | Shinbach | 206/620 |
| 4,609,578 | 9/1986 | Reed | 428/76 |
| 4,667,661 | 5/1987 | Scholz et al. | 128/90 |
| 4,668,563 | 5/1987 | Buese et al. | 428/230 |
| 4,696,404 | 9/1987 | Corella | 206/604 |
| 4,718,556 | 1/1988 | Hildebrandt | 206/604 |
| 4,720,366 | 1/1988 | Binnersley et al. | 264/172 |
| 4,769,202 | 9/1988 | Eroskey et al. | 264/166 |
| 4,774,937 | 10/1988 | Scholz et al. | 128/90 |
| 4,781,297 | 11/1988 | Abrahamsson et al. | 206/610 |
| 4,801,042 | 1/1989 | Hamada et al. | 220/410 |
| 4,834,245 | 5/1989 | Ohga et al. | 206/610 |
| 4,841,958 | 6/1989 | Ersfeld et al. | 128/90 |
| 4,883,625 | 11/1989 | Glemet et al. | 264/136 |
| 4,903,841 | 2/1990 | Ohsima et al. | 206/604 |
| 4,903,843 | 2/1990 | Fischer | 206/609 |
| 4,927,010 | 5/1990 | Kannankeril | 206/204 |
| 4,940,047 | 7/1990 | Richter et al. | 128/90 |
| 4,984,566 | 1/1991 | Sekimo et al. | 128/90 |
| 5,014,403 | 5/1991 | Buese | 28/170 |
| 5,027,803 | 7/1991 | Scholz et al. | 128/89 |
| 5,063,639 | 11/1991 | Boeckmann et al. | 24/30.5 |
| 5,127,065 | 6/1992 | Wade | 383/200 |
| 5,139,593 | 8/1992 | Loubineux et al. | 156/73.2 |
| 5,310,587 | 5/1994 | Akahori et al. | 428/35.2 |
| 5,346,939 | 9/1994 | Moren et al. | 524/176 |
| 5,353,486 | 10/1994 | Schmidt et al. | 28/167 |
| 5,454,601 | 10/1995 | Sekine et al. | 383/200 |
| 5,620,095 | 4/1997 | Delmore et al. | 383/201 |

EASY OPEN PACKAGE AND METHOD OF MAKING SAME

RELATED APPLICATIONS

This application is a continuation-in-part of U.S. Ser. Nos. 08/402,512, filed Mar. 10, 1995, U.S. Pat. No. 5,620,095, (allowed) and 08/075,663, filed Jun. 11, 1993, abandoned, which are herein incorporated by reference.

FIELD OF THE INVENTION

This invention relates to a package for an orthopedic casting article which may be easily torn open even when the outer surface of the package has been contacted with a lubricant. This invention also relates to methods of manufacturing easy opening packages.

BACKGROUND OF THE INVENTION

Many different orthopedic casting materials have been developed for use in the immobilization of broken or otherwise injured body limbs. Some of the first casting materials developed for this purpose involve the use of plaster of Paris bandages consisting of a mesh fabric (e.g., cotton gauze) with plaster incorporated into the openings and onto the surface of the mesh fabric. Plaster of Paris casts, however, have a number of attendant disadvantages, including a low strength-to-weight ratio, resulting in a finished cast which is very heavy and bulky. Furthermore, plaster of Paris casts typically disintegrate in water, thus making it necessary to avoid bathing, showering, or other activities involving contact with water. Such disadvantages, as well as others, stimulated research in the orthopedic casting art for casting materials having improved properties over plaster of Paris.

A significant advancement in the art was achieved when polyisocyanate prepolymers were found to be useful in formulating a resin for orthopedic casting materials, as disclosed, for example, in U.S. Pat. No. 4,502,479 (Garwood et al.) and U.S. Pat. No. 4,441,262 (Von Bonin et al.). U.S. Pat. No. 4,502,479 sets forth an orthopedic casting material comprising a knit fabric which is made from a high modulus fiber (e.g., fiberglass) impregnated with a polyisocyanate prepolymer resin such as polyurethane. Orthopedic casting materials made in accordance with U.S. Pat. No. 4,502,479 provide significant advancement over the plaster of Paris orthopedic casts, including a higher strength-to-weight ratio and greater air permeability. Since the polyisocyanate prepolymer resin is generally formulated to be activated with water the aforementioned casting products are often provided to the user in the form of a "kit" comprising an air and water impermeable package and a roll of casting tape therein. The package is generally constructed of a multilaminate film material.

U.S. Pat. No. 4,667,661 (Scholz et al.) discloses a casting tape which further comprises a lubricant. The lubricant serves to provide a casting material which after being dipped in water is easy to apply and slippery to mold without the resin sticking to the gloved hands of the applier.

Unfortunately, the lubricant upon contact with the package also makes the outer surface of the package slippery. This reduces the "grip" a user can achieve on the edges of the package when he or she attempts to tear open the package. In many cases the grip is so reduced that the user is unable to easily exert the necessary tear force. Therefore, in order to open the package the user must either change his gloves or completely wash his hands and/or the outer surface of the package. Alternatively, the user may opt to open several packages at once (i.e., before letting the lubricant contact his gloved hands) and avoid this "slip" problem. However, this method has the disadvantage that the user must estimate the number of rolls needed for a particular therapy before beginning the therapy. In the event that the number of rolls is underestimated the slippery problem is not avoided. In contrast, in the event that the number of rolls is overestimated these extra rolls are needlessly exposed to atmospheric moisture and premature cure, and are therefore wasted.

From the foregoing, it will be appreciated that what is needed in the art is a kit of orthopedic casting material which has both the advantages of a slippery resin and an easy open package which may be easily opened even when contacted by a lubricant. It would be a further advancement in the art to provide this kit in a cost effective manner. Such kits of orthopedic casting material and methods for preparing the same are disclosed and claimed herein.

SUMMARY OF THE INVENTION

The present invention relates to kits of orthopedic casting materials and methods for preparing and using such orthopedic casting materials, wherein the kit comprises: an orthopedic casting material comprising a curable liquid resin; a lubricant; and an air and water impermeable package comprising a friction region on the outer surface of the package and crossing a cut, wherein the friction region provides a sufficient static friction when the outer surface of the package has been contacted with a lubricant to facilitate easily tearing open the package. In one preferred embodiment of the present invention the friction region comprises a matte-finish label adhered to the outer surface of the package. In an alternative embodiment of the present invention the friction region comprises a plurality of small perforations through the outer surface of the package in the sealed region. If desired, both embodiments may be used together on one package.

The friction regions of the present invention are positioned to provide a sufficient grip for each hand (i.e., a separate grip region for each hand on each side of the cut) thereby allowing for the easy tearing of the sheet when a lubricant has contacted the package. More preferably, the friction regions, in addition to being on both sides of the cut, are positioned on both sides of the package (i.e., a first friction region on the thumb side of the package and a second friction region on the finger side of the package).

In one presently preferred embodiment of the present invention the friction regions are provided as a pair of matte-finish (i.e., non-glossy) paper "labels" adhered to the outer surface of the package. The labels are adhered to the package crossing a cut (e.g., using a pressure sensitive adhesive or a hot-melt rubber cement) and on opposite sides of the package. If desired a single suitable label may be wrapped or folded over the edge of the package and thereby adhere to both outer surfaces of the package (i.e., "on opposite sides" as previously mentioned).

In an alternative presently preferred embodiment of the present invention the friction regions are provided as a plurality of small perforations through the outer surface of the package in the sealed region. More preferably the perforations are placed in the sealed edge region of the package crossing a cut, with a portion of the perforations projecting through the package towards a first side of the package and a portion of the perforations projecting towards the opposite side of the package.

BRIEF DESCRIPTION OF THE DRAWINGS

Other advantages of the invention will become apparent from the following drawing where like numerals refer to like parts.

DETAILED DESCRIPTION OF THE INVENTION

The present invention relates to kits of orthopedic casting materials and methods for preparing and using such orthopedic casting materials, wherein the kit comprises an orthopedic casting material comprising a backing or fabric, preferably a stretchable backing or fabric, which is impregnated with a curable liquid resin, a lubricant, and an air and water impermeable package comprising a laminate sheet material and a means for facilitating tearing of the sheet material when the outer surface of the pouch has been contacted with the lubricant.

One element of this invention is a semi-rigid or flexible sheet upon which a curable resin can be associated to reinforce the sheet when the resin is cured thereon. The sheet is preferably porous such that the sheet is only partially impregnated with the resin. Examples of suitable sheets are non-woven, woven, or knit fabrics comprised of natural or synthetic fibers or materials. The sheet may alternatively be referred to as the "scrim" or the "backing." Suitable sheets which may be employed are knit fiberglass fabrics such as disclosed in U.S. Pat. Nos. 4,502,479; 4,609,578; 4,668,563; and 5,014,403 and in U.S. Pat. No. 5,353,486. Particularly preferred sheets of this type are extensible, heat-set fabrics as disclosed in U.S. Pat. No. 4,609,578 (Reed) which is herein incorporated by reference. One example of a knitted fiberglass scrim which is within the scope of U.S. Pat. No. 4,609,578 is known by 3M, St. Paul, Minn., as the Scotchcast™ 2 knitted fiberglass scrim. The Scotchcast™ 2 scrim is used in the manufacture of 3M's Scotchcast™ 2 and Scotchcast™ Plus orthopedic casting materials. Suitable non-fiberglass backings of the present invention include fabrics comprising: natural organic fibers; animal derived materials; naturally based organic polymer fibers; and synthetic polymer fibers. Suitable natural organic fibers for use in the fabric of the present invention include: vegetable derived materials such as abaca, cotton, flax, hemp, jute, kapok, linen, ramie, and sisal. Suitable animal derived materials include wool, mohair, vicuna, other animal hairs, and silk. Presently preferred organic fibers include: cotton and wool. Cotton is presently most preferred. Suitable naturally based organic polymers for use in the fabric of the present invention include: acetate, azion, rayon, and triacetate. Suitable synthetically prepared organic polymers include: acrylic, aramid, nylon, olefin (e.g., poly(1-butene), polyethylene, poly(3-methyl-1-butene), poly(1-pentene), polypropylene, and polystyrene), polyester, polytetrafluoroethylene, poly(vinyl alcohol), poly(vinyl chloride), and poly(vinylidine chloride). Presently preferred synthetic polymer fibers include: acrylic, nylon, polyethylene, polypropylene, polyester, and rayon. Presently most preferred synthetic polymer fibers include: nylon, polyester, and rayon. In this regard, preferred knitted, woven, or non-woven sheets made of organic fibers are described, for example, in U.S. Pat. Nos. 4,940,047; 4,984,566; and 4,841,958 (Ersfeld et al.) which are herein incorporated by reference.

A second element of this invention is a curable resin. The curable resins useful in this invention are resins which can be used to coat a sheet material and which can then be cured to reinforce the sheet material. The resin is curable to a crosslinked thermoset state. The preferred curable resins are fluids, i.e., compositions having viscosities between about 5 Pa s and about 500 Pa s, preferably about 10 Pa s to about 100 Pa s as measured at 23° C. using a Brookfield RVT Rotovisco viscometer.

The resin used in the casting material of the invention is preferably any curable resin which will satisfy the functional requirements of an orthopedic cast. Obviously, the resin must be nontoxic in the sense that it does not give off significant amounts of toxic vapors during curing which may be harmful to either the patient or the person applying the cast and also that it does not cause skin irritation either by chemical irritation or the generation of excessive heat during cure. Furthermore, the resin must be sufficiently reactive with the curing agent to insure rapid hardening of the cast once it is applied but not so reactive that it does not allow sufficient working time to apply and shape the cast. Initially, the casting material must be pliable and formable and should adhere to itself. Then in a short time following completion of cast application, it should become rigid or, at least, semi-rigid, and strong to support loads and stresses to which the cast is subjected by the activities of the wearer. Thus, the material must undergo a change of state from a fluid-like condition to a solid condition in a matter of minutes.

The preferred resins are those cured with water. Presently preferred are urethane resins cured by the reaction of a polyisocyanate and a polyol such as those disclosed in U.S. Pat. No. 4,131,114. A number of classes of water-curable resins known in the art are suitable, including polyurethanes, cyanoacrylate esters, and, when combined with moisture sensitive catalysts, epoxy resins and prepolymers terminated at their ends with trialkoxy- or trihalo-silane groups. For example, U.S. Pat. No. 3,932,526 discloses that 1,1-bis (perfluoromethylsulfonyl)-2-aryl ethylenes cause epoxy resins containing traces of moisture to become polymerized.

Resin systems other that those which are water-curable may be used, although the use of water to activate the hardening of an orthopedic casting tape is most convenient, safe and familiar to orthopedic surgeons and medical casting personnel. Resin systems such as that disclosed in U.S. Pat. No. 3,908,644 in which a bandage is impregnated with difunctional acrylates or methacrylates, such as the bis-methacrylate ester derived from the condensation of glycidyl methacrylate and bisphenol A (4,4'-isopropylidenediphenol) are suitable. The resin is hardened upon wetting with solutions of a tertiary amine and an organic peroxide. Also, the water may contain a catalyst. For example, U.S. Pat. No. 3,630,194 proposes an orthopedic tape impregnated with acrylamide monomers whose polymerization is initiated by dipping the bandage in an aqueous solution of oxidizing and reducing agents (known in the art as a redox initiator system). The strength, rigidity and rate of hardening of such a bandage is subjected to the factors disclosed herein.

Some presently more preferred resins for use in the present invention are water-curable, isocyanate-functional prepolymers. A water-curable isocyanate-functional prepolymer, as used herein, means a prepolymer derived from polyisocyanate, preferably aromatic, and a reactive hydrogen compound or oligomer. The prepolymer has sufficient isocyanate-functionality to cure upon exposure to water, e.g., moisture vapor, or preferably liquid water. Suitable systems of this type are disclosed, for example, in U.S. Pat. No. 4,411,262, and in U.S. Pat. No. 4,502,479. Presently more preferred resin systems are disclosed in U.S. Pat. No. 4,667,661 and U.S. patent application Ser. No. 07/376,421 which are herein incorporated by reference. The following disclosure relates primarily to the preferred embodiment of the invention wherein water-curable isocyanate-functional prepolymers are employed as the curable resin.

It is preferred to coat the resin onto the fabric as a polyisocyanate prepolymer formed by the reaction of an isocyanate and a polyol. It is preferred to use an isocyanate which has low volatility such as diphenylmethane diisocyanate (MDI) rather than a more volatile material such as toluene diisocyanate (TDI). Suitable isocyanates include 2,4-toluene diisocyanate, 2,6-toluene diisocyanate, mixture of these isomers, 4,4'-diphenylmethane diisocyanate, 2,4'-diphenylmethane diisocyanate, mixture of these isomers together with possible small quantities of 2,2'-diphenylmethane diisocyanate (typical of commercially available diphenylmethane diisocyanate), and aromatic polyisocyanates and their mixture such as are derived from phosgenation of the condensation product of aniline and formaldehyde. Typical polyols for use in the prepolymer system include polypropylene ether glycols (available from Arco Chemical under the trade name Arcol™ PPG and from BASF Wyandotte under the trade name Pluracol™), polytetramethylene ether glycols (Polymeg™ from the Quaker Oats Co.), polycaprolactone diols (Niax™ PCP series of polyols from Union Carbide), and polyester polyols (hydroxyl terminated polyesters obtained from esterification of dicarboxylic acids and diols such as the Rucoflex™ polyols available from Ruco division, Hooker Chemical Co.). By using high molecular weight polyols, the rigidity of the cured resin can be reduced.

An example of a resin useful in the casting material of the invention uses an isocyanate known as Isonate™ 2143L available from the Dow Chemical Company (a mixture of di- and tri-isocyanates containing about 73% of MDI) and a polypropylene oxide polyol from Union Carbide known as Niax™ PPG725. To prolong the shelf life of the material, it is preferred to include from 0.01 to 1.0 percent by weight of benzoyl chloride or another suitable stabilizer.

The reactivity of the resin once it is exposed to the water curing agent can be controlled by the use of a proper catalyst. The reactivity must not be so great that: (1) a hard film quickly forms on the resin surface preventing further penetration of the water into the bulk of the resin; or (2) the cast becomes rigid before the application and shaping is complete. Good results have been achieved using 4-[2-[1-methyl-2-(4-morpholinyl)ethoxy]ethyl]-morpholine (MEMPE) prepared as described in U.S. Pat. No. 4,705,840, the disclosure of which is incorporated by reference, at a concentration of about 0.05 to about 5 percent by weight.

Foaming of the resin should be minimized since it reduces the porosity of the cast and its overall strength. Foaming occurs because carbon dioxide is released when water reacts with isocyanate groups. One way to minimize foaming is to reduce the concentration of isocyanate groups in the prepolymer. However, to have reactivity, workability, and ultimate strength, an adequate concentration of isocyanate groups is necessary. Although foaming is less at low resin contents, adequate resin content is required for desirable cast characteristics such as strength and resistance to peeling. The most satisfactory method of minimizing foaming is to add a foam suppressor such as silicone Antifoam A (Dow Corning), or Anti-foam 1400 silicone fluid (Dow Corning) to the resin. It is especially preferred to use a silicone liquid such as Dow Corning Anti-foam 1400 at a concentration of about 0.05 to 1.0 percent by weight. Water-curable resins containing a stable dispersion of hydrophobic polymeric particles, such as disclosed in U.S. patent application Ser. No. 07/376,421 and laid open as European Published Patent Application EPO 0 407 056, may also be used to reduce foaming.

Also included as presently more preferred resins are the water reactive liquid organometallic compounds disclosed in U.S. Pat. No. 5,346,939, and the water curable alkoxy silane terminated oligomers disclosed in U.S. Pat. No. 5,423,735, which are herein incorporated by reference. These resins are especially preferred as an alternative to isocyanate resin systems.

The kits of orthopedic casting material of the present invention further comprise a lubricant for reducing the tack of the curable casting material (e.g., reducing the tack between the activated curable casting material and a gloved hand). The lubricant may be present in the kit as described in any one of the following embodiments. For example, the lubricant may be provided as part of the curable resin system, as a separate component which is added to the activator (e.g., added to a water dip), or as a coating to a glove which is designed to transfer lubricant to the activator or casting material during the activation of the resin and/or the wrapping of the cast. Alternatively, the lubricant may be provided as a coating to a glove that otherwise reduces the tack of the casting material by providing a slippery glove surface. As used herein a "kit" refers to a combination of articles or ingredients which are sold as a unit or a combination of articles or ingredients which are designed to be used together in a method of immobilizing a limb. For example, a "kit" includes the combination of a glove or a package of gloves comprising a lubricant and a package of the present invention containing a casting material.

In one preferred embodiment of the present invention the lubricant may be provided as part of the resin in accordance with U.S. Pat. No. 4,667,661, which is herein incorporated by reference, such that the casting materials exhibit reduced tack prior to and during cure and yet form a cast with acceptable strength and lamination strength. Suitable lubricants include: hydrophilic groups which are covalently bound to the resin system; additives which are incompatible with the curable resin including: a surfactant, a polymer comprised of a plurality of hydrophilic groups, and a polysiloxane; and combinations of the above.

When the lubricant is initially provided "inside" the package (e.g., associated with the casting material or otherwise sealed within the pouch) the outer surface of the first opened package is likely not to be contacted with lubricant prior to being opened. However, the utility of the present invention will readily be apparent when one attempts to open a second package. In this case the lubricant from the casting material of the first opened package is then available to contact the applier's gloves or mix with the activator solution, etc. The lubricant from the first opened package will then be available for contact with the outer surface of the second unopened package and thereby render the outer surface of the second package slippery. Alternatively, when the lubricant is initially provided "outside" the package (e.g., as a coating for a glove or as an additive to the activator solution) it is available for contact with the first opened package and can thereby render the outer surface of the first, and any subsequent, package slippery.

Figure 1:
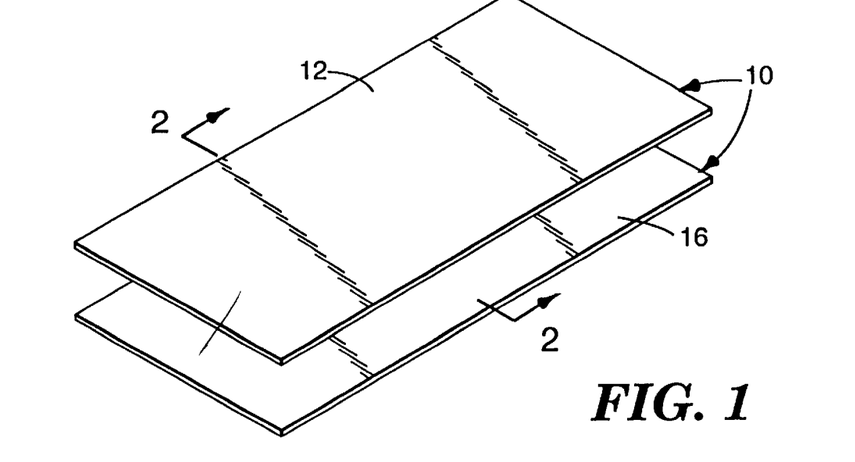
FIG. 1 is a fragmented, perspective view of a suitable laminate sheet material of the present invention.
Figure 2A:
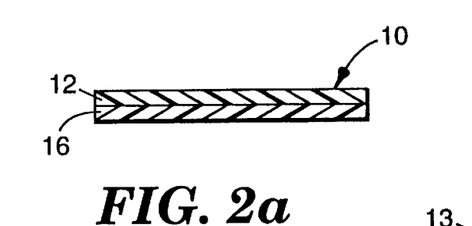
FIGS. 2a, 2b, and 2c are greatly enlarged cross-sectional views of the laminate sheet material of FIG. 1 taken approximately along the line 2—2 of FIG. 1.
Figure 2B:
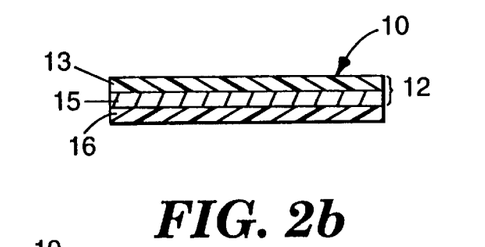
Figures 2C, 5:
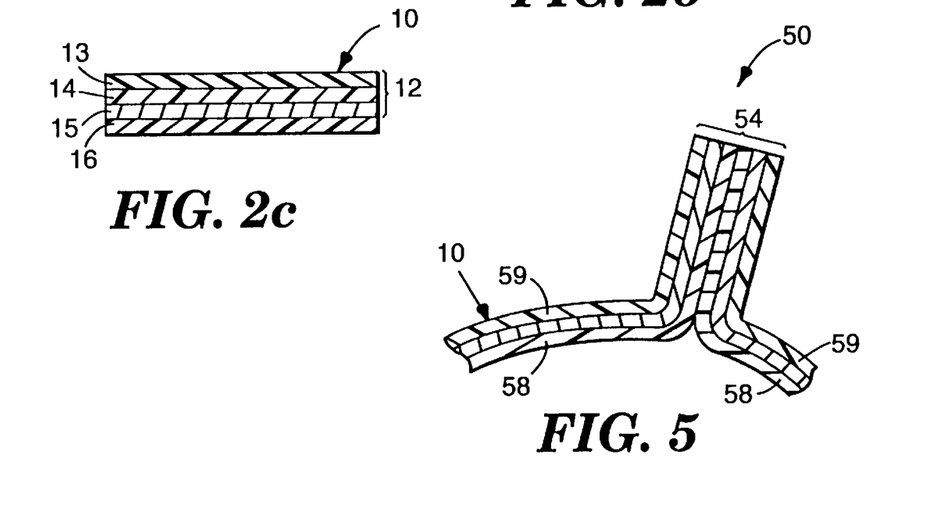
FIG. 5 is an enlarged, fragmented, cross-sectional view of the embodiment of FIG. 4 taken approximately along the line 5—5 of FIG. 4.

Referring now to FIGS. 1 and 2(a–c) of the drawings, there is shown, in perspective view in FIG. 1 and in cross-sectional view in FIGS. 2a, 2b, and 2c, a laminate sheet material 10 used to form the package of the present invention. As seen in FIG. 2a, the laminate sheet material 10 is comprised of an outer barrier film 12, and a heat-sealable inner film 16. As seen in FIG. 2b, the outer barrier film 12 is comprised of a puncture resistant outer material 13, and an intermediate layer 15. As seen in FIG. 2c, the laminate sheet material 10 further comprises a bonding layer 14 which serves to bond the outer material 13 and the intermediate layer 15.

The sheet material 10 is comprised of conventional materials that are pressure and/or adhesive laminated together in conventional fashion as will next be described. Intermediate layer 15 of sheet material 10 is preferably comprised of a metal foil that is highly impervious to air and water vapor. Preferably, the intermediate layer 15 is comprised of an aluminum foil having a thickness between 0.002 and 0.03 mm, more preferably between 0.005 and 0.015 mm, and most preferably between 0.007 and 0.010 mm. Although it is preferred that such aluminum foil be entirely free of even minute holes, it is known that such aluminum foil remains highly impervious to air and water vapor transmission even when having a few widely scattered, minute openings therethrough. By highly impervious, then, it is meant that as little as possible air and water vapor can pass through minute openings occurring in currently available metal foils. The outer barrier film 12 of the laminate sheet material 10 comprises a protective, puncture-resistant paper or plastic resin material. Preferably, the outer barrier film 12 is comprised of a polyester or a polypropylene film that is laminated to the aluminum foil of the intermediate layer 15 by conventional extrusion or adhesive bonding. For example, a bonding layer 14 may be utilized to bond the outer material 13 to the intermediate layer 15. Suitable bonding layer materials comprise low density polyethylene materials (hereinafter referred to as "LDPE") preferably having a density between 0.91 and 0.93 g/cc. The heat-sealable inner film 16 of the sheet material 10 is comprised of a heat-sealable material which can be laminated onto the aluminum foil of the intermediate layer 15 by adhesives, extrusion or the like. Preferably, the heat-sealable material is a plastic resin film such as a polypropylene, a polyethylene or a polyethylene-polypropylene copolymer that is extruded and/or calendered directly onto the aluminum foil. Most preferably, the heat-sealable material is "Surlyn"™ brand ionomer resin available from DuPont de Nemours & Co. (Inc.), Wilmington, Del. which is extruded and/or calendered directly onto the aluminum foil. Of related interest is the following U.S. patent application, filed on Jun. 11, 1993 by the assignee of this invention: Orthopedic Casting Material and Hermetic Package, Ser. No. 08/075,815 which is herein incorporated by reference.

Figures 3A, 3B, 4:
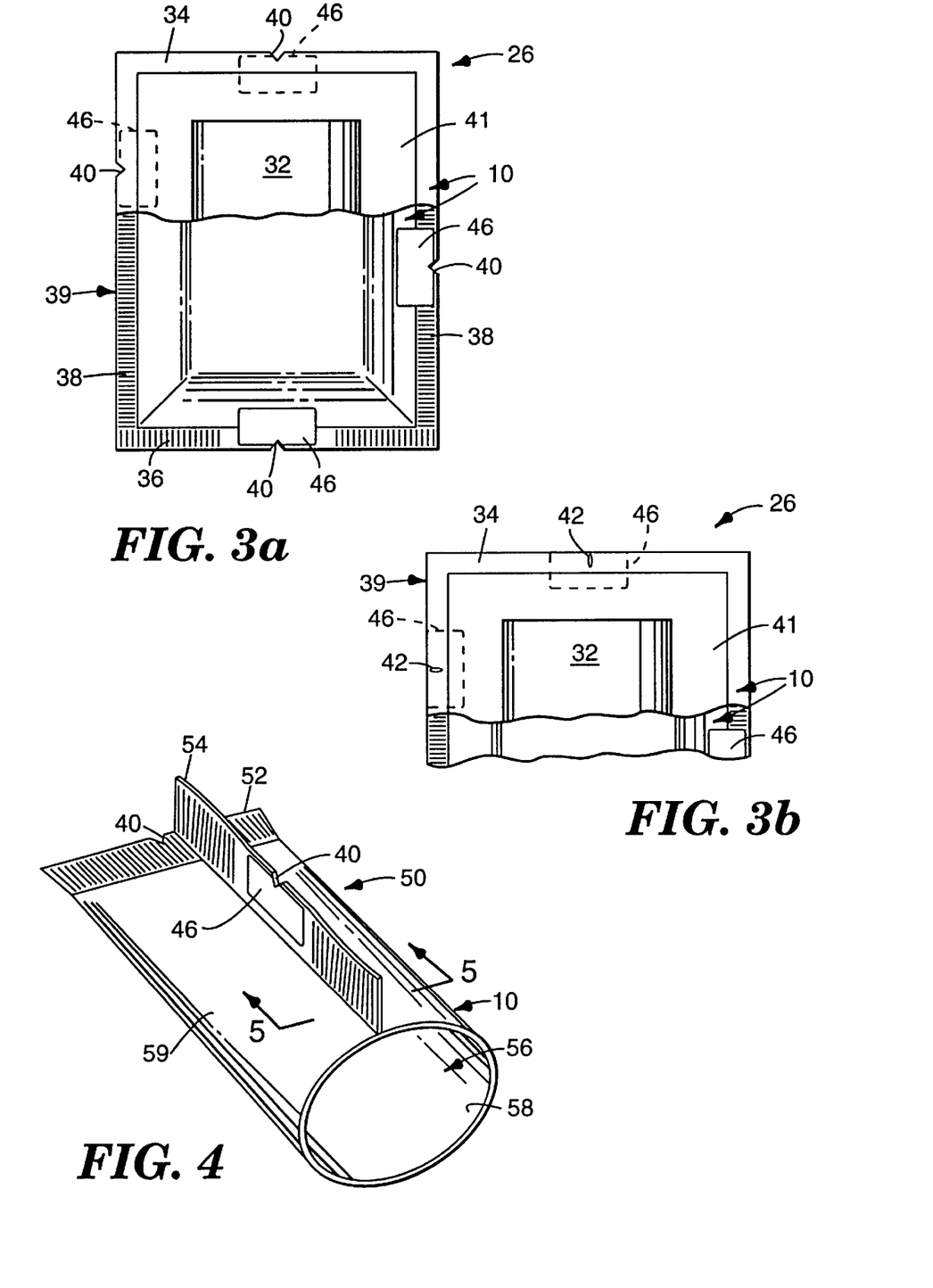
FIG. 3a is a plan view of one embodiment of the package of the present invention with portions broken away to show an object therein.
FIG. 3b is an enlarged, fragmented plan view depicting a cut wholly contained within the seal region.
FIG. 4 is a perspective view of an alternative embodiment of the package of the present invention.

FIG. 3a shows in plan view a first embodiment of a package 26 of the present invention formed from the laminate sheet material 10. The package 26 can be generally formed from a single piece of sheet material 10 or two pieces of sheet material 10. The package 26 is generally formed by peripherally heat sealing the sheet material 10 to itself or to a second piece of sheet material 10.

Still referring to FIG. 3a, there is shown the package 26 partially broken away to expose a sheet of curable casting material 32 otherwise hermetically sealed therein. As already described, the package 26 includes one or two pieces of sheet material 10 peripherally heat sealed together at two end heat seals 34 and 36 and two side heat seals 38 to form a pouch 39 having interior walls 41. The seals 34, 36, and 38 provide stiffened portions of the pouch 39 that are highly impervious to air and water vapor. By highly impervious, it is meant that as little as possible, and preferably no air and water vapor passes through these stiffened portions of the pouch 39.

Within one or more of the end heat seals 34 and 36 or the side heat seals 38 are one or more cuts 40 for facilitating the tearing of the package 26. Presently preferred cuts comprise a notch at the edge of the pouch in the seal region. The shape of the notch can be any shape (such as, for example, a "V" shaped notch or a thin slit) which effectively concentrates an applied stress and thereby facilitates the tearing or fracture of the laminate sheet material. Preferably, the cut is near the edge of the pouch. Alternatively, and as depicted in FIG. 3b, the cut 42 may be contained within a heat seal and not at the free edge of the package. In this embodiment (i.e., where the cut is near but not at the edge of the package) the cut serves to concentrate an applied stress at two points and thereby initiate two tears. The first tear propagates towards the edge of the package while the second tear propagates away from the edge of the package and thereby open the pouch portion.

FIGS. 4 and 5 of the drawings show an alternative embodiment of the package of the present invention. Referring first to FIG. 4, a package 50 is shown in perspective view to be generally of a conventional fin-seal construction. The package 50 is conventionally formed around the sheet of curable casting material 32, shown in FIG. 3, from a single sheet of laminate sheet material 10 to have a fin seal 54 and a first end heat seal 52 to form a pouch 56 containing the sheet of curable casting material 32. The fin seal 54 provides a stiffened portion of the pouch 56.

The pouch 56 has an interior wall 58 and an exterior wall 59. Within the heat seal 52 is a cut 40 (or alternatively 42) for facilitating tearing the package 50 of the embodiment. The package 50 is completed by heat sealing the pouch 56 at the end opposite the heat seal 52. In so doing, a second cut similar to the cut 40 can be provided. Alternatively, the cut may be provided along the aforementioned fin seal 54.

Near the aforementioned cut 40 or 42 are friction regions 46 adapted to the outer surface of the pouch. The friction region may be either a continuous region having a substantially uniform static coefficient of friction ("SCOF") over the region or a non-continuous region having areas of varying coefficients of friction. In general, the friction region should be large enough to provide a sufficient "grip" (i.e., total static friction) when a lubricated sheet is pressed between a thumb and finger to allow the sheet material to be torn. In particular, the grip provided by the friction region should be sufficient to facilitate the tearing of the package when the outer surface of the package has been contacted with the aforementioned lubricant.

Figure 6A:
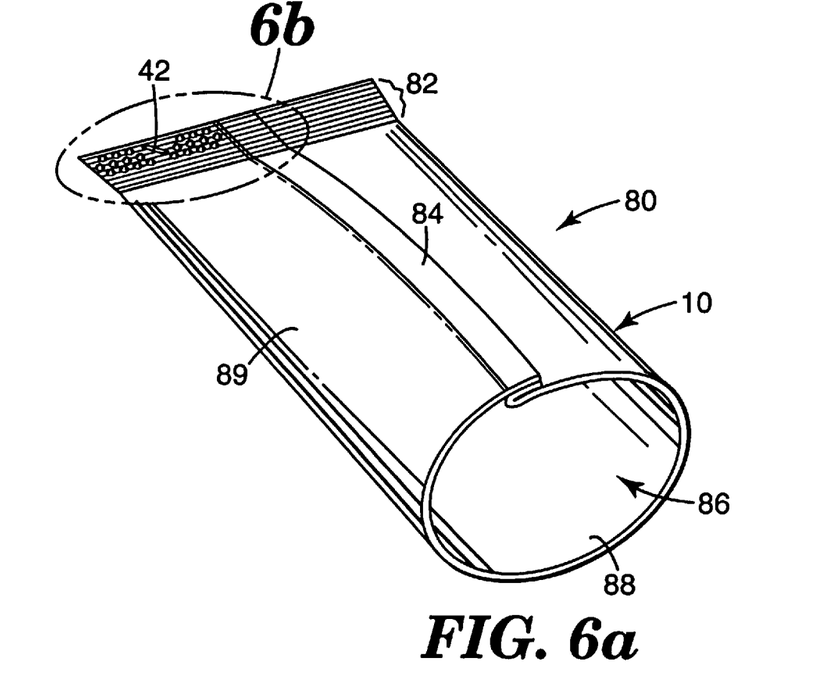
FIG. 6a is a perspective view of an alternative embodiment of the package of the present invention.
Figure 6B:
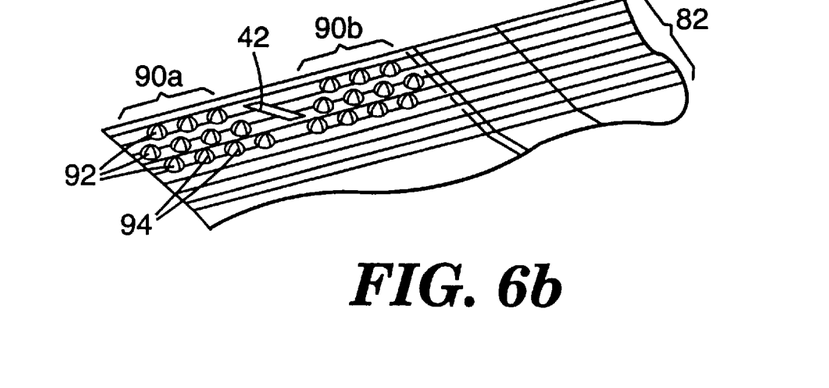
FIG. 6b is an enlarged view of the friction region of the package of FIG. 6a, showing a plurality of perforations through the sealed edge region of the package.

FIGS. 6a and 6b of the drawings show an alternative embodiment of the package of the present invention. Referring first to FIG. 6a, a package 80 is shown in perspective view to be of a conventional fin-seal construction. The package 80 is conventionally formed around the sheet of curable casting material 32, shown in FIG. 3, from a single sheet of laminate sheet material 10 to have a fin seal 84 and a first end heat seal 82 to form a pouch 86 containing the sheet of curable casting material 32.

The pouch 86 has an interior wall 88 and an exterior wall 89. Within the heat seal 82 is a cut 42 (or alternatively 40 as shown in FIG. 4) for facilitating tearing the package 80. The package 80 is completed by heat sealing the pouch 86 at the end opposite the heat seal 82.

Referring to FIG. 6b, an enlarged view of the friction region of FIG. 6a is shown. Near the aforementioned cut 42 are friction regions 90a and 90b comprising a plurality of perforations 92 which pass through the sealed region 82 of the package. In general, the friction region should be large enough to provide a sufficient "grip" when a lubricated sheet is pressed between a thumb and finger to allow the sheet material to be torn through the sealed region. In particular, the grip provided by the friction region should be sufficient to facilitate the tearing of the package when the outer surface of the package has been contacted with the aforementioned lubricant.

In a preferred embodiment the package contains at least four perforations on each side of the cut. The perforations 92 are preferably spaced apart in a manner so as to provide a region of a suitable size to grasp. More preferably, the package contains at least 8 perforation on each side of the cut. Most preferably, the package contains at least 10 perforation on each side of the cut. As shown in FIG. 6b the package contains eleven perforations on each side of the cut. If desired, a portion of the perforations may be formed so that the exposed edge of the packaging sheet 94 projects from opposite sides of the bag, thereby providing improved grip from both sides of the bag.

The size of the friction region should be large enough to provide the necessary static friction to achieve the tearing of the package. In general, the friction region is preferably as large as the contact area of the average human thumb and/or finger print. Preferably, the friction region has a minimum area on each side of the cut of at least 10 mm×10 mm, and more preferably at least 20 mm×20 mm. For friction regions that comprise a plurality of perforations the area shall be calculated as the overall area of the region that has the perforations. If desired, the friction region can be larger than this size and may encompass the total surface area of the package. However, for friction regions that comprise perforations, the perforations should be limited to the sealed region of the bag or outside the sealed region away from the pouch That is to say, no perforations should pass through the package material into the pouch portion. Furthermore, it is not intended that the geometry of the friction region be restricted to rectangular shapes. If desired circular, oval, triangular, or other geometries of similar surface area may be employed.

The friction region refers to that region on the outer surface of the package of the present invention which has a suitably high coefficient of friction to facilitate tearing of the package even when the friction region has been exposed or contacted with a lubricant as described herein. The friction region may comprise a separate layer or layers of a high coefficient of friction material bonded to the outer material 13; or may comprise an outer material having a suitably roughened outer surface; or may comprise a plurality of perforations through the sealed region of the package. Presently preferred are friction regions which comprise a separate layer of a suitable material (e.g., a material having a suitably high coefficient of friction) bonded to the outer material of the package. Also presently preferred are friction regions that comprise a plurality of perforations through the sealed region of the package.

Suitable friction region materials include label materials (e.g., adhesively backed paper materials), and texturized materials (e.g., texturized plastic materials, sandpaper, etc.). The friction region materials may be adhesively bonded or mechanically affixed to the laminate packaging material or incorporated directly into the laminate. Suitable label materials include matte-finished and gloss-finished paper materials. Although not intending to be bound by theory, gloss-finished paper materials are presently less preferred as the gloss-finish is believed to delay absorption of the lubricant solution and thus cause the gloss-finished material to initially present a relatively low static friction when contacted with a lubricant solution. In contrast, matte-finish paper materials provide high static friction immediately upon contact with the lubricant and are preferred for use in the present invention. If desired, gloss-finished paper materials may be utilized provided the user wait a period of time to let the necessary static friction develop. Preferred matte-finish label materials for use as the friction region include "Premium matte coated litho—permanent adhesive" C1S—available from Alford Label, Costa Mesa, Calif.

Suitable texturized materials include materials with perforated surfaces. One such perforated plastic tape is sold by 3M as TRANSPORE surgical tape. This tape comprises an extruded film backing and an adhesive layer. The film backing is approximately 0.01 cm thick. The tape is passed through an embossing station that creates a plurality of small perforations through the backing. The perforation have an average diameter of approximately 0.1 mm and are spaced in a rectangular array with approximately 100 perforations per square cm of tape.

If desired the texturized material may be formed directly in the packaging material. For example, suitable friction regions also include regions of the sealed seam of the package that have been perforated with a plurality of small holes. Preferred perforations create exposed foil surfaces 94 that improve the grip available to the user when wet or slippery hands are used to open the package. The perforations can be created during the production of the pouch by modifying the sealing apparatus that is used to form the pouch. This approach allows for the continuous production and filling of the pouch. Alternatively, the perforations may be formed using a separate tool after the pouch has been formed and the edges sealed. A suitable tool includes a pliers having modified jaws that comprise a pattern of projecting pins.

Suitable perforations are formed using tools having projections having a diameter between about 0.5 and 4 mm, more preferably between about 1 and 3 mm, and most preferably between about 1.5 to 2.5 mm. The perforations preferably are large enough that they cause an exposed edge 94 of the packaging laminate to project from the package. In other words, preferred perforations are formed using tools that not only create a bumpy surface on the surface of the package but also tear the laminate sheet material so as to expose an edge 94 of the laminate. The exposed edge may be similar in form to a "cheese grater" type structure. Alternatively, the exposed edge may comprise a single or multiple split of the "dome" of the projecting perforation.

The exact number of perforations will depend in part on the size of the perforations. For a perforation made using a pin of approximately 2 mm diameter, the preferred number of perforations on each side of the cut is between 8 and 16.

If desired, the perforations may be provided in addition to another suitable friction region material. For example, a matte-finished label or other texturized label may be applied to the package as previously discussed and a plurality of perforations may be provided through the label and the sealed region of the package.

Preferred friction regions should provide sufficient immediate static friction to allow tearing of the package when the package has been contacted with lubricant. By "immediate" static friction is meant that the material, when tested as described below, provides a sufficient static friction within 1 second of being contacted with the lubricant. Materials which develop sufficient static friction only after being exposed to the lubricant for a time period greater than 1 second are less preferred because the initial effort at tearing the package may result in a failure (i.e., the fingers may slip from the bag resulting in a dropped bag and possibly contamination of the sample).

The coefficient of friction of a material that has been contacted with a lubricant is determined as described below. For purposes of this invention the "grip" provided by the friction regions (herein referred to as the "total static friction") is the sum of the static frictions which are developed on each side of the package (i.e., one side of the package being in contact with a thumb of a hand and the other side being in contact with a finger, usually the forefinger, of the same hand). Each hand (i.e., each thumb and finger pressure pair) develops its own total static friction on each side of the cut and thereby imparts a tearing force. The lesser of the value of the total static friction of each hand is considered the total static friction of a friction region.

The friction regions of the present invention are positioned to provide a sufficient grip for each hand (i.e., a separate grip region for each hand on each side of the cut) thereby allowing for the easy tearing of the package sheet when a lubricant is contacting the package. More preferably, the friction regions, in addition to being on both sides of the cut, are positioned on both sides of the package (i.e., a first friction region on the thumb side of the package and a second friction region on the finger side of the package).

In one presently preferred embodiment of the present invention the friction regions are provided as a pair of matte-finish (non-glossy) paper "labels" adhered to the outer surface of the package. The labels are adhered to the package crossing a cut (e.g., using a pressure sensitive adhesive or a hot-melt rubber cement) and on opposite sides of the package. If desired a single suitable label may be wrapped or folded over the edge of the package and thereby adhere to both outer surfaces of the package (i.e., "on opposite sides" as previously mentioned). In an alternative preferred embodiment of the present invention the friction regions are provided as a region of perforations through the sealed region of the package.

As previously mentioned, the friction regions may be provided next to a cut at any convenient seam. Preferably, the cut and friction region are located near the middle of a seam so that the package is roughly torn in two equal halves.

It is anticipated that a minimum of one friction region that allows a suitable grip to be exerted on both sides of the cut be provided. Alternatively, the friction region may be provided on both sides of the package or at more than one cut. Alternatively, the friction regions may be positioned on opposite sides of the package such that a first friction region on the first side of the package provide a suitable grip on one side of the cut and a second friction region on the second side of the package provide a suitable grip on the other side of the cut.

FIGS. 3a and 3b show the position of cuts 40 and 42 on various seams of the package. At least one such cut is required. FIGS. 3a and 3b also show the position of the friction regions 46 that are positioned as described above on both sides of the cut and preferably on both sides of the package. The size of the friction regions depicted in FIGS. 3a and 3b are not intended to be limiting. If desired larger or smaller friction regions may be employed as discussed previously.

FIG. 4 shows an alternative embodiment of the present invention. The cut and friction regions may be on one or both of the end seals or on the fin seal.

The following examples are offered to aid in the understanding of the present invention and are not to be construed as limiting the scope thereof. Unless otherwise indicated, all parts and percentages are by weight.

EXAMPLES

Test for Determining the Static Coefficient of Friction

Determination of the frictional properties of many materials is often measured in terms of the coefficient of friction. This type of measurement may be made when sliding the material of interest over itself or over another object. The coefficient of friction is a dimensionless term which quantifies the frictional properties and may distinguish between surfaces of varying roughness, tackiness, slipperiness, etc. In the present application, a wide variety of lubricating properties are generated by surfactants or other surface active materials which are added either directly to the casting resins prior to coating the scrim or applied to precoated tape, etc. Although serving the primary purpose of reducing the tack between the casting material and the applier's hands or gloves the lubricants often come in contact with the outer surface of the air and water impermeable package that encloses the casting material. The lubricants have the undesirable effect of rendering the outer surface of the package slippery thereby making the package difficult to grip and tear open. The present invention provides a package of casting material comprising at least one friction region that allows a person to effectively "grip" the package and tear it open. By "grip" is meant the total static friction force produced on a sheet material by a person exerting a reasonable pressure (i.e., a comfortable pressure and not a painful pressure) between their opposing thumb and finger.

A test has been developed which measures the relative grip provided by the friction region, i.e., the static friction between the friction region and a latex glove material. This test method is based on ASTM test method D 1894-87 ("Static and Kinetic Coefficients of Friction of Plastic Film and Sheeting") and measures the static coefficient of friction between a horizontal stationary piece of test specimen and a 200 g 304 stainless steel sled covered with a latex coating. The procedure and apparatus of ASTM test method D 1894 have been modified as described herein. This method yields empirical data which, for the most part, correlates with actual performance of the friction region and thereby offers a quantitative measurement of the grip properties of a given friction region material (when contacted with a standard lubricant solution).

As used herein, the following terms have the following meanings:

"Static Friction"—the resisting or opposing force that arises when a surface of one object starts to slide over the surface of another object.

"Static Coefficient of Friction"—("SCOF") the ratio of the static frictional force to the force acting perpendicularly to the two surfaces in contact (usually the gravitational force). This dimensionless term is a measure of the relative difficulty with which the two materials will initially start to slide across one another i.e., the higher the static coefficient of friction the more difficult it is to start to slide the two materials over one another. The static coefficient of friction, as used herein, is determined from the test described hereinafter and is calculated by the equation:

$$SCOF = \frac{\text{force required to start the sled (g)}}{200 \text{ (g)}}$$

Test Method

SAMPLE AND MATERIALS CONDITIONING

Sample Conditioning—Test samples should be conditioned at 21–25° C. for not less than 1 hour prior to testing.

Water Conditioning—Water for use in this test should be deionized or soft water conditioned to 22–24° C.

Test Conditions—Testing must be conducted in a controlled temperature and humidity environment of 21–25° C. and 45–55% relative humidity.

APPARATUS

Sled—A 304 stainless steel half round cylinder 4.92 cm diameter by 2.54 cm wide and 2.54 cm high with a 4–40 0.5 inch thread in one end into which an Instron part no. T53-5 eye screw is fastened. Material is added or removed from the top of the sled so as to adjust the weight to 200±0.5 g. The radiused face of the sled is coated with a layer of double stick tape (#401 available from 3M, St. Paul, Minn.) which is then covered with a latex strip cut from a typical latex glove (Conform™ #69-205, available from Ansell Edmont Industries, Inc., Coshorton, Ohio).

Test Fixture—The Instron Coefficient of Friction Fixture (Catalog No. 2810-005) had previously been modified to accommodate testing of casting materials. Specifically, the pulley assembly was raised 2.54 cm and an additional Teflon™ coated brass tension pulley 0.953 cm in diameter× 13.34 cm was fixed to the end of the table opposite the load pulley and positioned such that the top of the pulley was in the plane of the table.

Force Measuring Device—An Instron Model No. 1122 table top measuring instrument equipped with a 222.4 Newton load cell (Instron assembly No. A-30-39) and connected to an Instron Microcon II microprocessor Model No. MC4100.

PREPARATION OF APPARATUS

1. Assemble the apparatus as described above.
2. Set the drive speed of the sled (i.e. the crosshead speed) to 127 cm/min.
3. Calibrate the 222.4 N load cell using a 500 g weight.
4. The following settings on the control panel of the Instron Model No. 1122 measuring device should be set: crosshead speed=127 cm/min; full scale load=0–22.24 N; chart speed=12.7 cm/min auto; load cell filter=in; polarity= up.
5. Set up the chart recorder to measure the peak tension force for travel between 0.0 and 2.54 cm.

PROCEDURE

The following procedure is appropriate for testing the static friction of various friction region materials which have been contacted with a lubricant. This procedure is also used to determine static coefficient of friction on "immediately" contacted materials by eliminating the 10 second waiting time after the material has been contacted with the lubricant solution (step #3). This procedure is not expected to be appropriate for testing the static friction of friction regions that comprise a plurality of perforations (i.e., perforations formed using 2 mm diameter pins.) The surface of such friction regions is not expected to be regular enough to provide a reliable static coefficient of friction measurement. For such friction regions one may simply test their effectiveness by lubricating the package with the solution mentioned below and then attempting to open the package using normally gloved hands.

1. Cut the friction region sample to obtain a strip having a width of at least 25.4 mm and a length of at least 50 mm. Place the sample flat on the testing table and fix one end into the hold down clamp.
2. Spray the surface of the sample with approximately 1.2 grams of a lubricant solution comprising 0.28 percent Pluronic™ F-108 in deionized water.
3. 10 seconds after the specimen has been contacted with the lubricant solution, gently place the sled on the specimen such that the wire is straight without sagging and under 10–15 g tension.
4. Within 1 seconds after the sled has been placed on the specimen start the driving mechanism which was previously adjusted to a crosshead speed of 127 cm/min.
5. Record the peak tension force for travel between 0.0 and 2.54 cm.
6. Remove the sled and immediately clean the sliding surface with a soft paper towel. Allow the sled to dry.

Example 1

Comparison of Static Friction of a Standard Outer Material and a Matte-finish Paper Friction Region Material Using the aforementioned test method the static coefficient of frictions of a standard packaging material and a matte-finish paper friction region material were measured.

A lubricating solution was prepared by mixing 1.4 gm Pluronic™ F-108 (available from BASF Wyandotte, Parsippany, N.J.) and 500 ml deionized water. This solution was formulated to provide to a non-slippery orthopedic casting material (such as Delta-Lite™ "S", available from the Johnson and Johnson Orthopaedics Inc., Raynham, Mass.) approximately the amount of lubrication that a typical non-tacky orthopedic casting material (such as Scotchcast™ Plus available from 3M, St. Paul, Minn.) exhibits when dipped in water and rubbed with a gloved hand. The lubricant solution was sprayed on the test material prior to measuring the frictional properties.

For this measurement the stainless steel sled was covered with a latex rubber surface. Thus the test apparatus measured the frictional properties between the test material and a latex glove material under conditions designed to simulate the actual "wet" conditions encountered when one tries to open a package that has been contacted with a lubricant (e.g., by contact with a wet glove that has been rubbing a slippery casting material from a previously opened roll or has been dipped into an activator solution containing a lubricant).

A sheet of standard packaging material was laid flat on the Instron Coefficient of Friction Fixture and tested as described herein. The sheet was a four ply laminate comprising one layer each of Surlyn™ #1652 ionomer resin, aluminum foil (0.089 mm thick), low density polyethylene, and polypropylene (0.0254 mm thick). The laminate was positioned in the fixture with the polypropylene layer facing up (i.e., the polypropylene layer was positioned to contact the sled). To the laminate was sprayed approximately 1.2 grams of the aforementioned lubricant solution. After waiting 10 seconds the latex coated sled was placed on the laminate and pulled across the laminate as described above. The mean static friction force of 10 runs was calculated to be 21.1 grams (standard deviation "$\sigma$"=3.45 grams).

A sample of a matte-finish label material (Premium matte coated litho—permanent adhesive" C1S, available from Alford Label, Costa Mesa, Calif.) was tested as described above for use as the friction region material. The label material is coated on one side with a pressure sensitive adhesive suitable for adhering the label to the outer surface of a standard packaging laminate. The label material was positioned and clamped in the test fixture with the matte-finish paper surface facing up (i.e., in position to contact the sled). After contact with the lubricant solution the latex coated sled and matte-finish material produced a mean static friction of 136.2 grams ($\sigma$=3.32 grams, n=11).

For comparison these same materials were tested wet but without exposure to the lubricant (i.e., a spray of plain water was employed). The standard laminate material produced a static friction of 183.8 grams ($\sigma$=16.42 grams, n=5) against the latex coated sled, while the matte-finish paper label material produced a static friction of 163.9 grams ($\sigma$=1.53 grams, n=5) against the latex coated sled.

The above data demonstrates that while both the standard package and the matte-finish label material provide good static friction when contacted with plain water the standard laminate material exhibits a large drop in static friction (hence loss of "grip") when contacted with a lubricant solution. In contrast, the matte-finish label material provides a good "grip" even when contacted with a lubricant solution.

Example 2

Comparison of "Immediate" Static Friction of a Standard Outer Material and a Matte-finish Paper Friction Region Material Using the aforementioned test method the immediate static coefficient of frictions of a standard packaging material and a matte-finish paper friction region material were measured.

A lubricating solution was prepared as described in Example 1. A sheet of standard packaging material was laid flat on the Instron Coefficient of Friction Fixture and tested as described herein. The sheet was a four ply laminate comprising one layer each of Surlyn™ #1652 ionomer resin, aluminum foil (0.089 mm thick), low density polyethylene, and polypropylene (0.0254 mm thick). The laminate was positioned in the fixture with the polypropylene layer facing up (i.e., the polypropylene layer was positioned to contact the sled). To the laminate was sprayed approximately 1.2 grams of the aforementioned lubricant solution. Without waiting the latex coated sled was immediately placed on the laminate and pulled across the laminate as described above. The mean immediate static friction force of 10 runs (10 separate samples of laminate material were tested) was calculated to be 31.2 grams ($\sigma$=11.9 grams).

A sample of a matte-finish label material (as described in Example 1) was tested as described above for use as the friction region material. The label material was positioned and clamped in the test fixture with the matte-finish paper surface facing up (i.e., in position to contact the sled). After contact with the lubricant solution the latex coated sled and matte-finish material produced a mean immediate static friction of 102.6 grams ($\sigma$=3.2 grams, n=10).

A sample of a gloss-finish label material ("Premium gloss coated litho—permanent adhesive" C1S, available from Alford Label, Costa Mesa, Calif.) was tested as described above for use as the friction region material. The label material was positioned and clamped in the test fixture with the gloss-finish paper surface facing up (i.e., in position to contact the sled). After contact with the lubricant solution the latex coated sled and gloss-finish material produced a mean immediate static friction of 63.5 grams ($\sigma$=6.3 grams, n=10).

The above data demonstrates that the gloss-finish label material provides a lower immediate static friction when contacted with a lubricant solution than a matte-finish material. Furthermore, the matte-finish label material provides a good immediate "grip" even when contacted with a lubricant solution.

Example 3

Package having a Plurality of Perforation Through a Sealed Region

A foil laminate package containing a 7.6 cm wide roll of SCOTCHCAST PLUS Casting Tape (Product # 82003, available from 3M) was modified in the following manner. To the end sealed region that contains a cut was added a plurality of perforations adjacent each side of the cut. The perforations were made through the sealed region using a modified set of pliers. The pliers were fitted with 85 mm wide jaws. One jaw was fitted with two arrays of eleven pins in a pattern as shown in FIG. 6b. The opposing jaw was fitted with receiving holes. The eleven pins of each region were arranged in three rows. A first row had three pins, spaced approximately 4 mm apart. The second and third rows had four pins each. The pins of the second row were staggered from those of the first and third row. It is understood that the number, size, and arrangement of the pins can be varied without departing from the scope of this invention.

The pins used to make the perforations were made using rod bar stock (2.35 mm in diameter) the sides of which had been ground to produce a four sided point. The resulting perforations in the package had a base of about 2 mm diameter and project about 1 mm from the surface of the package. In many instances the perforations resembled a dome having a split through its surface. The split reveals an edge of the laminate and provides a gripping surface.

On a separate package, perforations were alternatively made using the tip of a small "Phillips" type screwdriver. The tip was pushed through the laminate far enough to create a perforation that resembled a dome with a "+" tear through its surface. By rotating the tip the perforation can be spread opened even more completely, thereby exposing more edge of the laminate.

Various modifications and alterations of this invention will be apparent to those skilled in the art without departing from the scope and spirit of this invention, and it should be understood that this invention is not limited to the illustrative embodiments set forth herein.

What is claimed is:

1. A kit, comprising:
    an orthopedic casting material having a curable resin;
    a lubricant for reducing the tack between the resin and the hand of the applier of the casting material; and an air and water impermeable package, wherein the package comprises at least one friction region positioned on the outer surface of the package and a cut located near the edge of the package and near the friction region for facilitating tearing the package, wherein the friction region provides a mean immediate total static friction of at least 100 grams when contacted with a lubricant, and wherein the curable casting material is adapted to fit inside the package.

2. A kit according to claim 1, wherein the package comprises a laminate sheet material comprising a heat-sealable plastic inner film, a metal foil and a puncture resistant outer material laminated to at least one major surface of the metal foil.

3. A kit according to claim 1, wherein the friction region is adapted to both outer surfaces of the package.

4. A kit according to claim 1, wherein the friction region provides a mean immediate total static friction of at least 150 grams when contacted with a lubricant.

5. A kit according to claim 1, wherein the friction region comprises a label material having a surface area of at least 100 square mm and wherein the label crosses the cut.

6. A kit according to claim 1, wherein the label material comprises a matte-finish paper material.

7. A kit, comprising:

an orthopedic casting material having a curable resin;

a lubricant for reducing the tack between the resin and the hand of the applier of the casting material; and an air and water impermeable package, wherein the package comprises at least one friction region and a cut located near the sealed edge of the package for facilitating tearing the package, wherein the friction region is positioned near the cut and comprises a texturized material, and wherein the sheet of curable casting material is adapted to fit inside the package.

8. A kit according to claim 7, wherein the package comprises a laminate sheet material comprising a heat-sealable plastic inner film, a metal foil and a puncture resistant outer material laminated to at least one major surface of the metal foil.

9. A package suitable for containing an orthopedic casting material, comprising:

an air and water impermeable laminate sheet material comprising an outer barrier film, wherein the outer barrier film comprises a metal foil and a puncture resistant outer material laminated to at least one major surface of the metal foil, and a heat-sealable plastic inner film laminated to a major surface of the barrier film, the heat-sealable plastic inner film including sealed portions forming a pouch of the laminate sheet material, the pouch having at least one interior wall and at least one exterior wall, and wherein the sealed portions are highly impervious to air and water vapor; and a means for facilitating tearing of the sheet material when the outer surface of the package is contacted with a lubricant comprising at least one friction region and a cut located near the sealed edge of the package for facilitating tearing the pouch, wherein the friction region is positioned near the cut and comprises a plurality of perforations through a sealed seam of the package, and wherein the sheet of curable casting material is adapted to fit inside the pouch.

10. A package according to claim 9, wherein the friction region comprises at least 8 perforations through a sealed seam of the package.

11. A package according to claim 9, wherein the package comprises at least 8 perforations on each side of the cut.

12. A package according to claim 9, wherein the friction region has an overall surface area of at least 100 square mm and wherein the friction region crosses the cut.

13. A kit, comprising:

an orthopedic casting material having a curable resin;

a lubricant for reducing the tack between the resin and the hand of the applier of the casting material; and the package of claim 9.

14. A kit according to claim 13, wherein the friction region comprises at least 8 perforations, has an overall surface area of at least 100 square mm, and crosses the cut.

* * * * *